United States Patent [19]
Foerster et al.

[11] Patent Number: 5,902,310
[45] Date of Patent: May 11, 1999

[54] APPARATUS AND METHOD FOR MARKING TISSUE

[75] Inventors: Seth A. Foerster, San Clemente; Mark Cole, Santa Ana; Eugene B. Reu, Mission Viejo; Mark A. Ritchart, Murrieta; John L. Wardle, San Clemente, all of Calif.

[73] Assignee: Ethicon Endo-Surgery, Inc., Cincinnati, Ohio

[21] Appl. No.: 08/802,958

[22] Filed: Feb. 21, 1997

Related U.S. Application Data

[60] Provisional application No. 60/023,883, Aug. 12, 1996.

[51] Int. Cl.$^6$ .................................... A61B 17/10
[52] U.S. Cl. ...................... 606/142; 606/151; 606/219
[58] Field of Search ..................... 606/142, 143, 606/216, 219, 75, 151, 116, 117

[56] References Cited

U.S. PATENT DOCUMENTS

| | | |
|---|---|---|
| Re. 34,936 | 5/1995 | Campbell et al. . |
| 3,120,230 | 2/1964 | Skoid . |
| 3,915,162 | 10/1975 | Miller . |
| 3,958,576 | 5/1976 | Komiya . |
| 4,080,959 | 3/1978 | Leveen . |
| 4,103,690 | 8/1978 | Harris . |
| 4,583,538 | 4/1986 | Onik et al. . |
| 4,649,151 | 3/1987 | Dougherty et al. . |
| 4,682,606 | 7/1987 | DeCaprio . |
| 4,693,237 | 9/1987 | Hoffman et al. . |
| 4,733,664 | 3/1988 | Kirsch et al. . |
| 4,853,210 | 8/1989 | Kass . |
| 4,881,551 | 11/1989 | Taylor . |
| 4,907,599 | 3/1990 | Taylor . |
| 4,909,250 | 3/1990 | Smith . |
| 4,929,240 | 5/1990 | Kirsch et al. . |
| 4,994,069 | 2/1991 | Ritchart et al. . |

(List continued on next page.)

FOREIGN PATENT DOCUMENTS

| | | |
|---|---|---|
| 0146699 | 7/1985 | European Pat. Off. . |
| 0293605 | 12/1988 | European Pat. Off. . |
| 0350043 | 1/1990 | European Pat. Off. . |
| 0481685 | 4/1992 | European Pat. Off. . |
| 2132091 | 7/1984 | United Kingdom . |
| WO 90/05491 | 5/1990 | WIPO . |
| 9015576 | 12/1990 | WIPO . |
| 9319803 | 10/1993 | WIPO . |

OTHER PUBLICATIONS

S.S. Kramer et al;"A Permanent Radiopaque Marker Technique for the Study of Phayngeal Swallowing in Dogs"; *Dysphagia* vol., pp. 163–167 (1987).

Homer et al; "The Geographic Cluster of Microcalcifications of the Breast",*Surgery, Gynecology & Obstetrics,* Dec. (1985).

Finan et al; "Interstitial Radiotherapy for Early Stage Vaginal Cancer"; *The Journal of Reproductive Medicine;* vol. 38, No.3/Mar. 1993.

*Primary Examiner*—Michael Buiz
*Assistant Examiner*—Julian W. Woo
*Attorney, Agent, or Firm*—Matthew S. Goodwin

[57] ABSTRACT

An implantable marking device is provided which is designed to percutaneously deliver permanent markers to desired tissue locations within a patient's body, even if the desired locations are laterally disposed relative to the distal end of the delivery device, as is the case for conduit or cavity walls. This provides several advantages to the physician in diagnosis and management of tissue abnormalities, such as a means of localization of a tissue abnormality for follow-up surgical treatment, and a means of tissue abnormality site identification for purposes of ongoing diagnostic follow-up. In one preferred construction, a radiographic clip is configured in the form of a surgical staple. A disposable tissue marker applier, which comprises a flexible tube, pull wire, and squeeze handle, is employed to advance and deploy the clip to a desired tissue location. Either a flexible or a rigid introducer is also provided for providing access to the site to be marked.

45 Claims, 3 Drawing Sheets

U.S. PATENT DOCUMENTS

| | | |
|---|---|---|
| 5,018,530 | 5/1991 | Rank et al. . |
| 5,025,797 | 6/1991 | Baran . |
| 5,108,407 | 4/1992 | Geremia et al. . |
| 5,125,413 | 6/1992 | Baran . |
| 5,127,916 | 7/1992 | Spencer et al. . |
| 5,147,307 | 9/1992 | Gluck . |
| 5,156,609 | 10/1992 | Nakao et al. . |
| 5,188,111 | 2/1993 | Yates et al. . |
| 5,192,270 | 3/1993 | Carswell, Jr. . |
| 5,195,540 | 3/1993 | Shiber . |
| 5,197,482 | 3/1993 | Rank et al. . |
| 5,201,314 | 4/1993 | Bosley et al. . |
| 5,209,232 | 5/1993 | Levene . |
| 5,221,269 | 6/1993 | Miller et al. . |
| 5,226,911 | 7/1993 | Chee et al. . |
| 5,234,426 | 8/1993 | Rank et al. . |
| 5,242,456 | 9/1993 | Nash et al. . |
| 5,242,457 | 9/1993 | Akopov et al. . |
| 5,280,457 | 1/1994 | Figueroa et al. . |
| 5,342,283 | 8/1994 | Good . |
| 5,364,406 | 11/1994 | Sewell, Jr. . |
| 5,400,798 | 3/1995 | Baran . |
| 5,411,522 | 5/1995 | Trott . |
| 5,413,584 | 5/1995 | Schulze . |
| 5,445,167 | 8/1995 | Yoon et al. ............................ 606/143 |

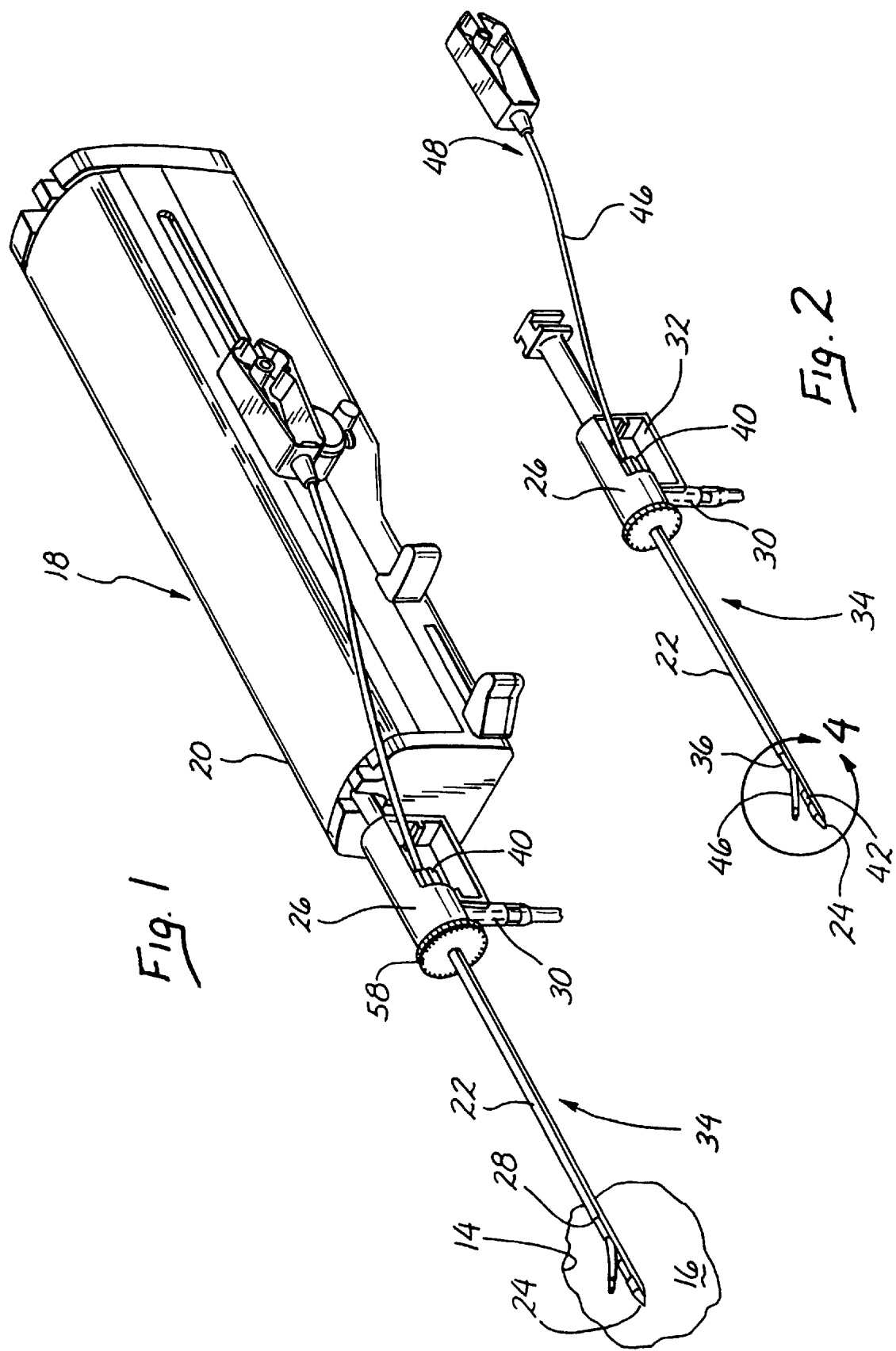

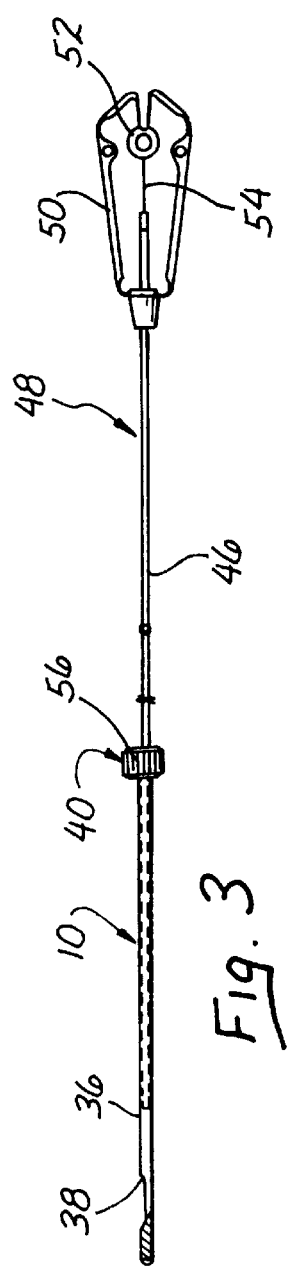
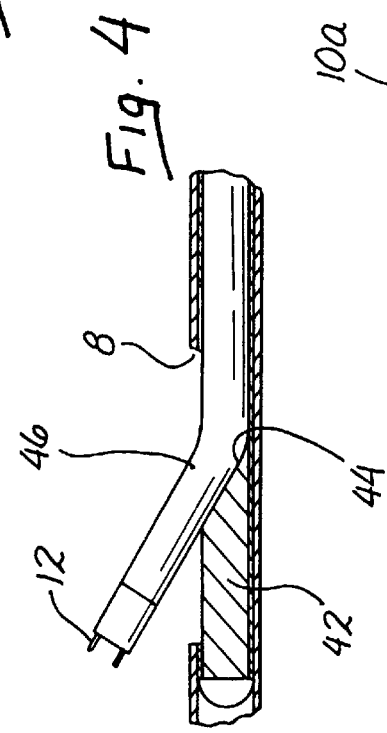
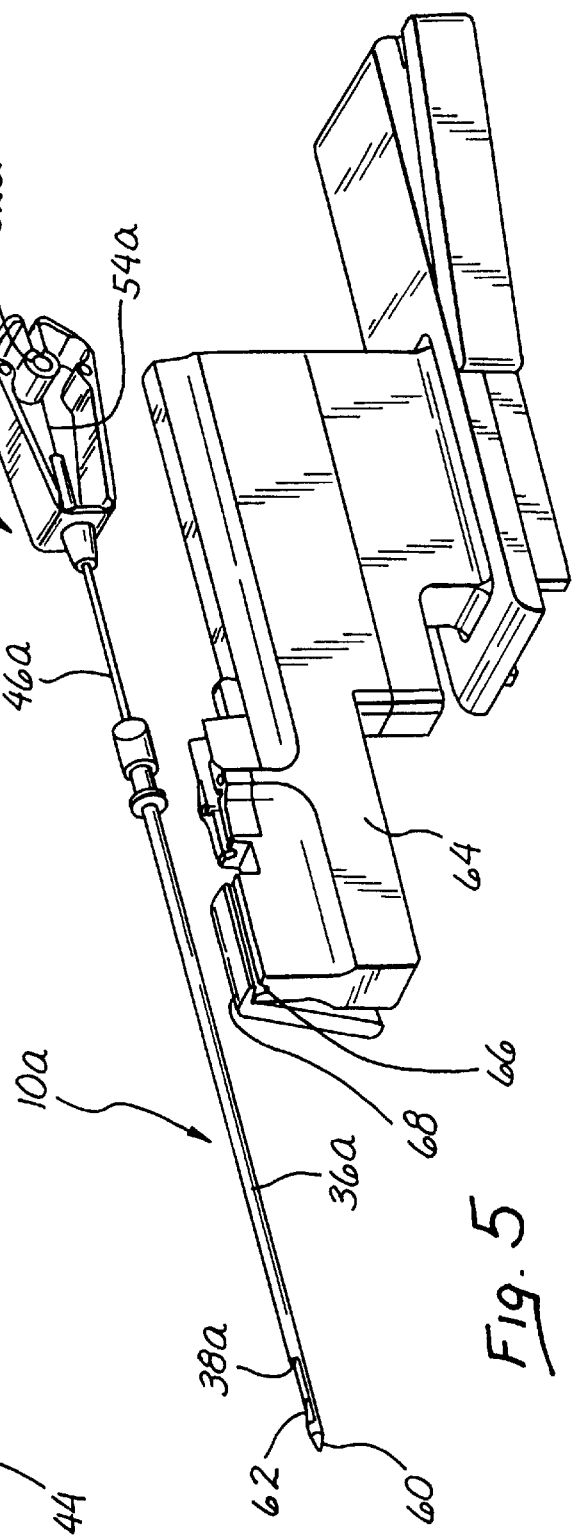

APPARATUS AND METHOD FOR MARKING TISSUE

CROSS-REFERENCE TO RELATED APPLICATIONS

This application claims the benefit under 35 U.S.C. 119(e) of U.S. Provisional patent application Ser. No. 60/023,883, filed on Aug. 12, 1996. The application is also related to co-pending application Ser. No. 08/308,097, entitled Methods and Devices for Defining and Marking Tissue, and filed on Sep. 16, 1994, which application is herein expressly incorporated by reference.

BACKGROUND OF THE INVENTION

This invention relates to methods and devices for marking and defining particular locations in body tissue, particularly human tissue, and more particularly relates to methods and devices for permanently defining the location and margins of lesions detected in biopsy cavity walls.

It is desirable and often necessary to perform procedures for detecting, sampling, and testing lesions and other abnormalities in the tissue of humans and other animals, particularly in the diagnosis and treatment of patients with cancerous tumors, pre-malignant conditions and other diseases or disorders. Typically, in the case of cancer, when a physician establishes by means of known procedures (i.e. palpation, x-ray, MRI, or ultrasound imaging) that suspicious circumstances exist, a biopsy is performed to determine whether the cells are cancerous. Biopsy may be an open or percutaneous technique. Open biopsy removes the entire mass (excisional biopsy) or a part of the mass (incisional biopsy). Percutaneous biopsy on the other hand is usually done with a needle-like instrument and may be either a fine needle aspiration (FNA) or a core biopsy. In FNA biopsy, very small needles are used to obtain individual cells or clusters of cells for cytologic examination. The cells may be prepared such as in a Papanicolaou (Pap) smear. In core biopsy, as the term suggests, a core or fragment of tissue is obtained for histologic examination which may be done via a frozen section or paraffin section. The chief difference between FNA and core biopsy is the size of the tissue sample taken. A real time or near real time imaging system having stereoscopic capabilities, such as the stereotactic guidance system described in U.S. Pat. No. 5,240,011, is employed to guide the extraction instrument to the lesion. Advantageous methods and devices for performing core biopsies are described in the assignee's U.S. Pat. No. 5,526,822 and co-pending patent applications Ser. No. 08/386,941, filed on Feb. 10, 1995; Ser. No. 08/568,143, filed on Dec. 6, 1995; and Ser. No. 08/645,225, filed on May 13, 1996. All of these patents and applications are herein expressly incorporated by reference.

Depending upon the procedure being performed, it is sometimes desirable to completely remove suspicious lesions for evaluation, while in other instances it may be desirable to remove only a sample from the lesion. In the former case, a major problem is the ability to define the margins of the lesions at all times during the extraction process. Visibility of the lesion by the imaging system may be hampered because of the distortion created by the extraction process itself as well as associated bleeding in the surrounding tissues. Although the lesion is removed and all fluids are continuously aspirated from the extraction site, it is likely that the process will "cloud" the lesion, thus impairing exact recognition of its margins. This makes it difficult to ensure that the entire lesion will be removed.

Often, the lesion is merely a calcification derived from dead abnormal tissue, which may be cancerous or pre-cancerous, and it is desirable to remove only a sample of the lesion, rather than the entire lesion, to evaluate it. This is because such a lesion actually serves to mark or define the location of adjacent abnormal tissue, so the physician does not wish to remove the entire lesion and thereby lose a critical means for later re-locating the affected tissue. One of the benefits to the patient from core biopsy is that the mass of the tissue taken is relatively small. However, oftentimes, either inadvertently or because the lesion is too small, the entire lesion is removed for evaluation, even though it is desired to remove only a portion. Then, if subsequent analysis indicates the tissue to be malignant (malignant tissue requires removal, days or weeks later, of tissue around the immediate site of the original biopsy), it is difficult for the physician to determine the precise location of the lesion, in order to perform necessary additional procedures on adjacent potentially cancerous tissue. Additionally, even if the lesion is found to be benign, there will be no evidence of its location during future examinations to mark the location of the previously removed calcification so that the affected tissue may be carefully monitored for future reoccurrences.

Thus, it would be of considerable benefit to be able to permanently mark the location or margins of such a lesion prior to or immediately after removing or sampling same. Marking prior to removal would help to ensure that the entire lesion is excised, if desired. Alternatively, if the lesion were inadvertently removed in its entirety, marking the biopsy site immediately after the procedure would enable reestablishment of its location for future identification.

A number of procedures and devices for marking and locating particular tissue locations are known in the prior art. For example, location wire guides, such as that described in U.S. Pat. No. 5,221,269 to Miller et al, are well known for locating lesions, particularly in the breast. The device described by Miller comprises a tubular introducer needle and an attached wire guide, which has at its distal end a helical coil configuration for locking into position about the targeted lesion. The needle is introduced into the breast and guided to the lesion site by an imaging system of a known type, for example, x-ray, ultrasound, or magnetic resonance imaging (MRI), at which time the helical coil at the distal end is deployed about the lesion. Then, the needle may be removed from the wire guide, which remains in a locked position distally about the lesion for guiding a surgeon down the wire to the lesion site during subsequent surgery. While such a location system is effective, it is obviously intended and designed to be only temporary, and is removed once the surgery or other procedure has been completed.

Other devices are known for marking external regions of a patient's skin. For example, U.S. Pat. No. 5,192,270 to Carswell, Jr. discloses a syringe which dispenses a colorant to give a visual indication on the surface of the skin of the point at which an injection has or will be given. Similarly, U.S. Pat. No. 5,147,307 to Gluck discloses a device which has patterning elements for impressing a temporary mark in a patient's skin, for guiding the location of an injection or the like. It is also known to tape or otherwise adhere a small metallic marker, e.g. a 3 millimeter diameter lead sphere, on the skin of a human breast in order to delineate the location of skin calcifications (see Homer et al, The Geogrephic Cluster of Microcalcifications of the Breast, *Surgery, Gynecology,* & *Obstetrics,* December 1985). Obviously, however, none of these approaches are useful for marking and delineating internal tissue abnormalities, such as lesions or tumors.

Still another approach for marking potential lesions and tumors of the breast is described in U.S. Pat. No. 4,080,959. In the described procedure, the skin of the portion of the body to be evaluated, such as the breasts, is coated with a heat sensitive color-responsive chemical, after which that portion of the body is heated with penetrating radiation such as diathermy. Then, the coated body portion is scanned for color changes which would indicate hot spots beneath the skin surface. These so-called hot spots may represent a tumor or lesion, which does not dissipate heat as rapidly because of its relatively poor blood circulation (about 1/20 of the blood flow through normal body tissue). This method, of course, functions as a temporary diagnostic tool, rather than a permanent means for delineating the location of a tumor or lesion.

A method of identifying and treating abnormal neoplastic tissue or pathogens within the body is described in U.S. Pat. No. 4,649,151 to Dougherty et al. In this method, a tumor-selective photosensitizing drug is introduced into a patient's body, where it is cleared from normal tissue faster than it is cleared from abnormal tissue. After the drug has cleared normal tissue but before it has cleared abnormal neoplastic tissue, the abnormal neoplastic tissue may be located by the luminescence of the drug within the abnormal tissue. The fluorescence may be observed with low intensity light, some of which is within the drug's absorbance spectrum, or higher intensity light, a portion of which is not in the drug's absorbance spectrum. Once detected, the tissue may be destroyed by further application of higher intensity light having a frequency within the absorbance spectrum of the drug. Of course, this method also is only a temporary means for marking the abnormal tissue, since eventually the drug will clear from even the abnormal tissue. Additionally, once the abnormal tissue has been destroyed during treatment, the marker is destroyed as well.

It is also known to employ biocompatible dyes or stains to mark breast lesions. First, a syringe containing the colorant is guided to a detected lesion, using an imaging system. Later, during the extraction procedure, the surgeon harvests a tissue sample from the stained tissue. However, while such staining techniques can be effective, it is difficult to precisely localize the stain. Also, the stains are difficult to detect fluoroscopically and may not always be permanent.

Additionally, it is known to implant markers directly into a patient's body using invasive surgical techniques. For example, during a coronary artery bypass graft (CABG), which of course constitutes open heart surgery, it is common practice to surgically apply one or more radiopaque rings to the aorta at the site of the graft. This enables a practitioner to later return to the site of the graft by identifying the rings, for evaluative purposes. It is also common practice to mark a surgical site with staples, vascular clips, and the like, for the purpose of future evaluation of the site.

A technique has been described for the study of pharyngeal swallowing in dogs, which involves permanently implanting steel marker beads in the submucosa of the pharynx (S. S. Kramer et al, A Pennanent Radiopaque Maker Technique for the Study of Phalynged Swadlowing in Dogs, *Dysphagia*, Vol. 1, pp. 163–167, 1987). The article posits that the radiographic study of these marker beads during swallowing, on many occasions over a substantial period of time, provides a better understanding of the pharyngeal phase of degluitition in humans. In the described technique, the beads were deposited using a metal needle cannula having an internal diameter slightly smaller than the beads to be implanted. When suction was applied to the cannula, the bead sat firmly on the tip. Once the ball-tipped cannula was inserted through tissue, the suction was broken, thereby releasing the bead, and the cannula withdrawn.

Accordingly, what is needed is a method and device for non-surgically implanting potentially permanent markers at the situs of a lesion or other abnormal tissue, for the purpose of defining the margins of a lesion before it is removed and/or to establish its location after it has been removed. The markers should be easy to deploy and easily detected using state of the art imaging techniques.

SUMMARY OF THE INVENTION

This invention solves the problems noted above by providing an implantable marking device which is designed to percutaneously deliver permanent markers to desired tissue locations within a patient's body, even if the desired locations are laterally disposed relative to the distal end of the delivery device, as is the case for conduit or cavity walls. The device allows the physician to accurately position and deploy a radiographic clip at the site of a biopsy. This provides several advantages to the physician in diagnosis and management of tissue abnormalities, such as a means of localization of a tissue abnormality for follow-up surgical treatment, and a means of tissue abnormality site identification for purposes of ongoing diagnostic follow-up. It may also prevent inadvertent repeat biopsy of a lesion if the patient were to move or if adequate records did not follow the patient. The inventive system also represents a less traumatic means for tissue marking and a reduced procedural duration relative to the standard open surgical method.

A second aspect of the inventive system comprises a unique tissue marker delivery assembly, available from the present assignee, Biopsys Medical, Inc. This assembly includes a radiographic clip that is configured in the form of a surgical staple. Also incorporated in the tissue marker assembly is a disposable applier. The applier provides a flexible tube, deployment mechanism, and squeeze handle as a means to advance and deploy the clip to a desired tissue location.

In a first embodiment of the invention, a flexible tissue marker introducer is employed. The flexible tissue marker introducer incorporates a flexible tube that allows the physician to access and deliver the tissue marker through a cassette housing on the biopsy probe. Additionally, the introducer employs a distal tip ramp feature which enables the tissue marker to be advanced laterally out of a laterally facing sample notch at a distal end of the biopsy probe, so that the tissue marker can be fixed to the side wall of the tissue cavity. One important inventive feature is the inclusion of an orientation mark on the hub of the introducer to allow the physician to obtain the desired placement position at the biopsy site.

In a second embodiment of the invention, a rigid introducer is utilized rather than a flexible introducer, so that the biopsy power driver and probe is not necessary to provide a rigid fixed position access channel for the marker delivery system. This embodiment is particularly useful when the biopsy power driver and probe being used is too small to accommodate the aforementioned flexible introducer, and an alternate access and delivery means is required. The rigid introducer of the invention may be utilized with or without a distal end ramp feature, depending upon whether lateral deployment of the marker is required.

The invention, together with additional features and advantages thereof, may best be understood by reference to the following description taken in conjunction with the accompanying illustrative drawing.

BRIEF DESCRIPTION OF THE DRAWING

FIG. 1 is a perspective view of a first embodiment of the invention, illustrating an arrangement for delivering and deploying a tissue marker through a flexible introducer, utilizing a motor-driven biopsy probe of known construction as an access conduit;

FIG. 2 is a perspective view similar to FIG. 1, wherein the driver portion of the motor-driven biopsy probe has been deleted in order to better isolate the flexible introducer and tissue marker applier;

FIG. 3 is a side elevational view of the flexible introducer and tissue marker applier illustrated in FIGS. 1 and 2;

FIG. 4 is a cross-sectional view of the distal end portion 4—4 of the flexible introducer illustrated in FIG. 3;

FIG. 5 is a perspective view of a second embodiment of the present invention, illustrating an arrangement for delivering and deploying a tissue marker through a rigid introducer;

DETAILED DESCRIPTION OF THE INVENTION

Figure 6:
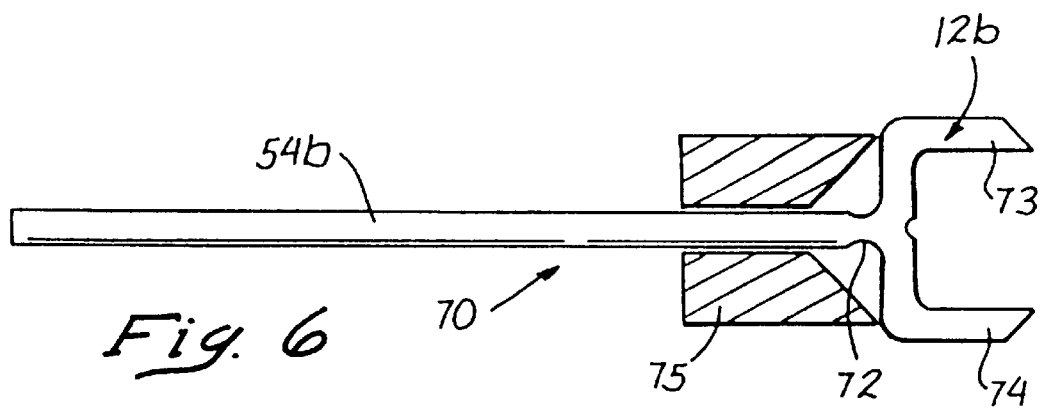
FIG. 6 is a cross-sectional view of a one-piece marking device constructed in accordance with the principles of the present invention.

Referring now more particularly to FIGS. 1–4, a first embodiment of an introducer 10 (best seen in FIG. 3) for delivering tissue markers 12 (FIG. 4) to a wall 14 of a biopsy cavity 16 is illustrated. As discussed in related application Ser. No. 08/308,097, tissue markers 12 are preferably comprised of a non-magnetic, radiographic material, and are preferably constructed in the form of a clip, or surgical staple, to facilitate attachment to the tissue they are intended to identify and to provide an easily recognized shape which would not be mistaken for another lesion. In the preferred embodiment, the maximum width of a tissue marker 12 is within a range of approximately 0.030 inches –0.050 inches, and preferably about 0.039 inches (1 mm). To place the marker 12 at a desired tissue location, a biopsy power driver and probe 18 is preferably used, such as the MAMMO-TOME® power driver and probe manufactured and sold by Biopsys Medical, Inc., of Irvine, Calif. the assignee of the present application. As described, for example, in U.S. Pat. No. 5,526,822, previously incorporated herein by reference, the biopsy power driver and probe 18 comprises a driver housing 20, a hollow outer piercing needle 22 having a distal piercing end 24, and a tissue cassette housing 26. The hollow outer piercing needle 22 includes a laterally facing tissue receiving port 28 near its distal end. The biopsy power driver and probe 18 is operated to obtain a tissue sample by first moving the distal piercing end 24 of the needle 22 into position to pierce the lesion or selected tissue which is to be sampled, using a known imaging device, such as a stereotactic imaging unit. Then, a vacuum may be drawn through a vacuum port 30 (FIG. 1) of the tissue cassette housing 26, and through the hollow needle 22 to create a negative pressure condition at the tissue receiving port 28, thereby drawing tissue into the port, where it is severed by an inner cutting cannula to capture a tissue sample. The tissue that is captured within the inner cutting cannula is transported proximally in an intact fashion by retracting the cutting cannula (not shown) rearwardly, preferably to a slot 32 (FIG. 2) in the tissue cassette housing 26. A plurality of tissue samples, from different orientations in the vicinity of the tissue receiving port 28, may be obtained without withdrawing the needle 22.

Once the desired tissue samples have been captured, thereby creating the biopsy cavity 16, it is often desirable to accurately position and deploy a permanent marker at the site of the biopsy. This provides several advantages to the physician in diagnosis and management of tissue abnormalities. For example, suitable permanent marking of the biopsy site provides a means for relocalizing the area of a tissue abnormality for follow-up surgical treatment, in the event the biopsy pathological results are positive. It also provides a means of tissue abnormality site identification for the purpose of ongoing diagnostic follow-up. To implant a marker in the cavity walls 14, however, requires a marker delivery system which permits accurate lateral discharge of the marker.

The present invention is particularly advantageous in that it utilizes the lumen of the hollow outer piercing needle 22 as the marker delivery conduit. Thus, subsequent to the biopsy procedure, while the probe 34 (FIG. 2) is still inserted within the patient's body at the biopsy site, it may be utilized as a fixed position, rigid, annular conduit for delivery and deployment of the tissue marker 12. The fact that the probe 34 never leaves the biopsy site ensures accurate delivery of the marker to the cavity 16, while also providing a less traumatic and quicker tissue marking process than the standard open surgical methods.

With particular reference now to FIG. 3, the flexible introducer 10 of the present invention is illustrated. The introducer 10 comprises a flexible tube 36 having an opening 38 adjacent to its distal end and a hub 40 at its proximal end. As illustrated in FIG. 4, a plug 42 is disposed at the distal end of the flexible tube 36, which plug includes an angled, sloping ramp 44 on a proximal end face thereof. The flexible tube 36 of the flexible introducer 10 is adapted to receive a flexible tube or deployment shaft 46 of a disposable tissue marker applier 48. The applier 48 comprises a squeeze handle 50 on its proximal end, which has a ring 52 to which is attached a pull wire 54. The pull wire 54 extends through the lumen of the deployment shaft 46, and is attached at its distal end to the marker 12 (FIG. 4).

To deploy a marker 12 into the cavity wall 14, the flexible tube 36 of the introducer 10 is inserted into the hollow needle 22 of the probe 34 through the tissue cassette housing 26, until the hub 40 abuts the tissue cassette housing 26, as illustrated in FIGS. 1 and 2. Once fully inserted, the hub 40 is rotated by the physician until an indexing mark or notch 56 (FIG. 3) is properly oriented, thereby ensuring that the introducer 10 is circumferentially aligned within the probe 34.

After the flexible tube 36 of the flexible introducer 10 has been inserted into the probe 34 and properly oriented, in the manner described above, the tissue marker applier 48 may be advanced into the lumen of the introducer 10, as illustrated in FIGS. 1 and 2, so that the distal end thereof exits from the notch 38 and tissue receiving port 28, extending into the cavity 16 (alternatively, the applier 48 may be first inserted into the introducer, and then the introducer may be inserted into the probe 34, if desired). An important aspect of the invention is the use of the ramp 44 to direct the flexible deployment shaft 46 radially outwardly from the notch 38 so that the marker 12 disposed at the distal end of the shaft 46 may be laterally transported to the cavity wall 14 for placement. Once the marker 12 is disposed at a desired marking location, the squeeze handle 50 is squeezed by the physician so that the pull wire 54 is retracted by the squeezing motion sufficiently to break the pull wire, thus releasing the marker 12 for implantation into the target tissue 14.

Once the marker has been implanted, the flexible deployment shaft 46 may be withdrawn from the introducer 10 and discarded, while a new applier 48 is inserted into the introducer to implant a second marker. As many markers as desired may be implanted, following which the hub 40 may be counter-rotated 90–270 degrees and the entire probe 34 withdrawn from the patient. If it is desired to mark various locations about the cavity wall 14, the probe needle 22 may be rotated between marker implantations to change the orientation of the tissue receiving port 28, using the thumbwheel 58. Additionally, the axial position of the port 28 may be adjusted, if desired.

Referring now to FIG. 5, a second embodiment of the inventive introducer mechanism is illustrated. In this embodiment, like elements to those of the first embodiment are designated by like reference numerals, followed by the letter a.

The significant difference between the first embodiment, illustrated in FIGS. 1–4, and the embodiment of FIG. 5, is that the introducer 10a is rigid, rather than flexible. The flexible introducer 10 of the first embodiment is adapted for use with a biopsy power driver and probe 18, which functions as the access mechanism. Therefore, the flexible characteristic of the tube 36 is necessary in order to facilitate threading of the tube 36 through the lumen of the needle 22, via the tissue cassette housing 26. This embodiment works very well in connection with larger sized probes, such as 11 gauge MAMMOTOME probes manufactured by Biopsys Medical, Inc., the present assignee, for example. However, the flexible tube 36 is too large to be threaded through smaller probes, such as the 14 gauge MAMMOTOME probe manufactured by the present assignee. Therefore, the second embodiment has been developed to provide a stand alone access device for introducing the tissue marker applier 48a.

The rigid introducer 10a illustrated in FIG. 5 comprises a rigid tube 36a having a piercing distal end 60, a distal laterally facing opening 38a, and a ramp 62. Since, in this embodiment, the introducer is not delivered through another access device, but rather is itself an access device, it is preferably loaded onto an introducer needle mount 64, so that the shaft 36a is disposed in a shaft channel 66 of the mount 64, and held in position by means of cover portion 68. The biopsy probe and driver 18 are removed from the imaging system (not shown), typically a stereotactic table available from Fischer Imaging, Inc. or from Lorad, Inc. The probe guide holder (not shown) is replaced by the loaded introducer needle mount 64. The introducer is then advanced to the desired tissue sampling site, following which the tissue marker applier is inserted through the introducer cannula to an appropriate depth mark to allow the distal tip clip to extend over the ramp 62 and to extend laterally sufficiently far to pierce tissue. The handle 50a is then squeezed in the manner discussed supra to deploy the distal tip clip 12. Then, the disposable applier is removed.

Alternatively, the introducer 10a may be utilized without the ramp 62, in the case where lateral placement of the marker with respect to the introducer 10a is not required.

Figure 7:
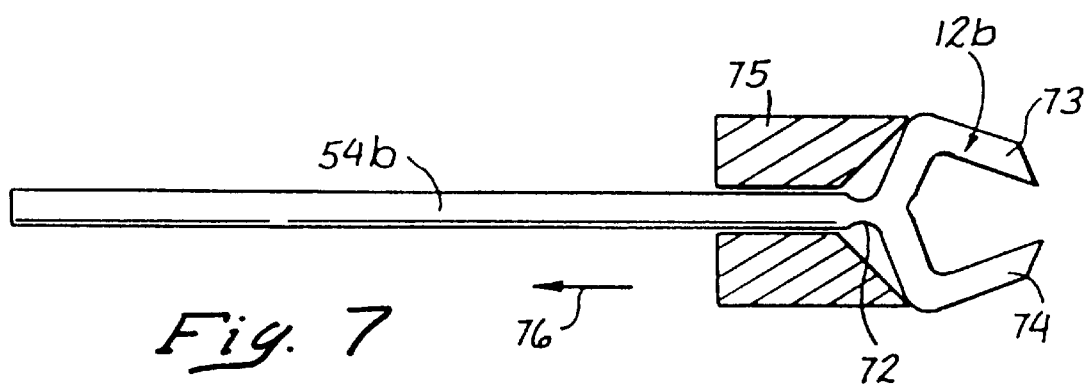
FIG. 7 is a cross-sectional view similar to FIG. 6, illustrating the one-piece marking device as the marker thereof is being pulled back against the forming die for partially closing the marker.
Figure 8:
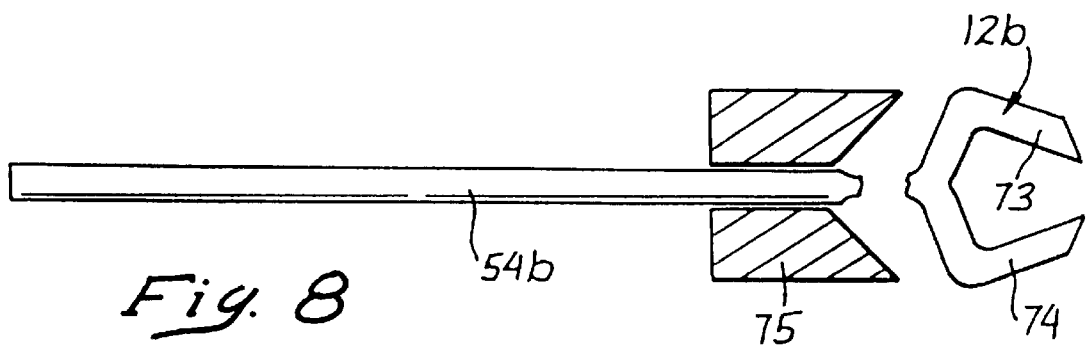
FIG. 8 is a cross-sectional view similar to FIG. 7, illustrating the marker as it is separated from the remainder of the marking device and deployed to mark a desired tissue site.

A particularly advantageous embodiment of the present invention is the employment of a one-piece marking element 70 (FIGS. 6–8), comprising a marker 12b and a marker closing ribbon or pull wire 54b which are comprised of a single piece of wire. In this particular marker embodiment, the single piece marking element 70 is preferably fabricated of a single piece of sheet material, ideally using a photo-chemical etching process to eliminate any fabrication and thermal stresses from being introduced into the part. The single-piece element is fabricated such that a weak spot or failure point 72 (FIGS. 6–7) is disposed at a location on the marking element which will break at a predetermined load after the legs 73, 74 of the marker have closed down and gripped the tissue to which the marker 12b is to be attached. Thus, as illustrated in FIGS. 6–8, a forming die 75 is provided which is disposed proximally of the marker portion 12b of the single-piece marking element 70. The failure point 72 is disposed between the forming die 75 and the marker 12b, at the distal end of the pull wire 54b. To deploy the marker 12b into the target tissue, a pulling force is applied proximally to the pull wire 54b, in the direction shown by arrow 76. This pulling force may be applied, for example, by a squeeze handle 50 like that shown in FIGS. 1–3 and 5, or by some other means. This proximal pulling force causes the marker portion 12b to travel proxally to a point where it impacts the distal end of the forming die 75, as illustrated in FIG. 7. Continued proximal pulling forces on the pull wire 54b results in closure forces being applied against the legs 73, 74 of the marker portion 12b. Ultimately, as illustrated in FIG. 8, continued application of a proximal pulling force on the pull wire 54b will result in breakage of the pull wire 54b at the failure point 72, so that the marker 12b becomes separated therefrom, with the legs 73, 74 of the marker being closed upon the tissue desired to be marked.

Figure 9:
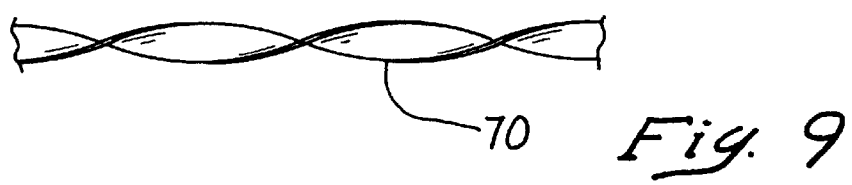
FIG. 9 is a schematic view illustrating a portion of the length of a pull wire which is constructed of twisted rectangular stock, in accordance with one of the principles of the present invention.

While the inventive marking element may be round in cross-section, in its preferred embodiment, the marking element 70 is fabricated of rectangular stock, which has been clamped at each end and twisted along its length (FIG. 9). The inventors have found that, absent the twisting step, the sharp edges of the rectangular stock tend to snag against the sides of the tube 46 (FIG. 3) as it is being pulled therethrough. Twisting, on the other hand, has been found to soften the edges of the stock sufficiently to ease passage of the pull wire 54b through the tube.

While this invention has been described with respect to various specific examples and embodiments, it is to be understood that the invention is not limited thereto and that it can be variously practiced within the scope of the following claims.

What is claimed is:

1. A one-piece marking apparatus for defining a particular tissue location, comprising:

a marker element; and a pull wire having a distal end and a proximal end, the marker element being attached to the distal end of the pull wire, wherein the marker element and the pull wire are comprised of a single piece of rectangular stock:

wherein said rectangular stock is twisted.

2. The one-piece marking apparatus recited in claim 1, and further comprising a forming die disposed proximally of said marker element, the marker element comprising first and second legs and the forming die comprising first and second forming faces corresponding to each of said first and second legs, such that when said pull wire is pulled in a proximal direction, said first and second legs are pulled proximally against said first and second forming faces of said forming die.

3. The one-piece marking apparatus recited in claim 2, and further comprising a predesigned failure point disposed in the distal end of said pull wire, just proximal to said marker element, wherein when the pull wire is pulled in a proximal direction, said first and second legs are pulled proximally against said first and second forming faces such that said legs close inwardly toward one another, attaching to adjacent tissue to be marked as they close, the proximal pulling force on said pull wire causing said predesigned failure point to yield when said marker element is attached to said tissue so that said marker element and said pull wire become separated from one another.

4. The one-piece marking apparatus recited in claim 1, and further comprising a predesigned failure point disposed in the distal end of said pull wire, just proximal to said marker, said failure point being adapted to fail, separating said marker element from said pull wire, upon application of a predetermined pulling force on said pull wire.

5. The one-piece marking apparatus recited in claim 1, wherein said single piece of sheet material comprises rectangular stock.

6. The one-piece marking apparatus recited in claim 1, wherein said marker element has a width of less than 0.1 inches.

7. The one-piece marking apparatus recited in claim 6, wherein said marker element has a maximum width within a range of 0.030–0.050 inches.

8. A method of making a marking apparatus for defining a particular tissue location, comprising the steps of:
    providing a single piece of sheet material having a proximal end and a distal end;
    forming a marker element having first and second legs on said distal end; and
    providing a predesigned failure point in said sheet material just proximal to said marker, said failure point being engineered to fail when a predetermined pulling force is applied on the proximal end of said single piece of sheet material, thereby separating the marker element from the remainder of the marking apparatus.

9. The method of making a marking apparatus as recited in claim 8, wherein the step of providing a single piece of sheet material includes providing a single piece of rectangular stock.

10. The method of making a marking apparatus as recited in claim 9, and further comprising the step of clamping the single piece of rectangular stock at both ends and twisting said rectangular stock.

11. The method of making a marking apparatus as recited in claim 8, wherein the step of providing a single piece of sheet material includes the step of using a photochemical etching process to fabricate the one-piece marking apparatus.

12. A device for marking a particular tissue area within a body to identify said particular tissue area for a later diagnostic or therapeutic procedure, comprising:
    a marker element;
    a flexible marker element applier for remotely delivering said marker element from outside the body to the particular tissue area, comprising an introducer having a tube, wherein the tube has a lumen, a distal opening and a proximal hub, and further comprising a flexible deployment shaft having a lumen, a distal end, and a proximal end;
    a handle on the proximal end of the flexible deployment shaft;
    wherein the flexible marker element applier further comprises a pull wire attached to said handle, the wire extending distally through the lumen of said flexible deployment shaft, a distal end of the pull wire being attached to said marker element, such that when said handle is actuated, a proximal pulling force is exerted by the handle on said pull wire.

13. The device for marking a particular tissue area as recited in claim 12, said handle comprising a squeeze handle, wherein said handle is actuated by a squeezing action to cause a proximal pulling force to be exerted on said pull wire.

14. The device for marking a particular tissue area as recited in claim 12, wherein the marker element and the pull wire are comprised of a single piece of sheet material.

15. The device for marking a particular tissue area as recited in claim 14, and further comprising a forming die disposed proximally of said marker element, the marker element comprising first and second legs and the forming die comprising first and second forming faces corresponding to each of said first and second legs, such that when said pull wire is pulled in a proximal direction, said first and second legs are pulled proximally against said first and second forming faces of said forming die.

16. The device for marking a particular tissue area as recited in claim 15, and further comprising a predesigned failure point disposed in the distal end of said pull wire, just proximal to said marker element, wherein when the pull wire is pulled in a proximal direction, said first and second legs are pulled proximally against said first and second forming faces such that said legs close inwardly toward one another, attaching to adjacent tissue to be marked as they close, the proximal pulling force on said pull wire causing said predesigned failure point to yield when said marker element is attached to said tissue so that said marker element and said pull wire become separated from one another.

17. The device for marking a particular tissue area as recited in claim 14, and further comprising a predesigned failure point disposed in the distal end of said pull wire, just proximal to said marker, said failure point being adapted to fail, separating said marker element from said pull wire, upon application of a predetermined pulling force on said pull wire.

18. The device for marking a particular tissue area as recited in claim 14, wherein said single piece of sheet material comprises rectangular stock.

19. The device for marking a particular tissue area as recited in claim 18, wherein said rectangular stock is twisted.

20. The device for marking a particular tissue area as recited in claim 12, wherein said marker element has a width of less than 0.1 inches.

21. The device for marking a particular tissue area as recited in claim 20, wherein said marker element has a maximum width within a range of 0.030–0.050 inches.

22. The device for marking a particular tissue area as recited in claim 12, wherein the distal opening on the introducer tube is oriented laterally.

23. The device for marking a particular tissue area as recited in claim 12, wherein said proximal hub includes a means for indexing the circumferential orientation of the introducer.

24. The device for marking a particular tissue area as recited in claim 12, wherein said flexible deployment shaft is insertable through the lumen of said introducer tube for transporting said marker element to said particular tissue area.

25. The device for marking a particular tissue area as recited in claim 24, wherein the introducer tube is comprised of a flexible material.

26. The device for marking a particular tissue area as recited in claim 25, said device further comprising a rigid annular conduit having a distal opening, said rigid annular conduit being adapted for entry into said body using an aided visualization device, wherein the distal opening of the conduit is disposed adjacent to said particular tissue area, said flexible introducer tube being insertable into said rigid annular conduit such that the distal end of the flexible introducer tube exits said rigid annular conduit through the distal opening thereof, thereby transporting said marker element to said particular tissue area.

27. The device for marking a particular tissue area as recited in claim 25, and further comprising an angled ramp disposed at the distal end of the flexible introducer tube, adjacent to the distal opening on said tube, said ramp functioning to cause said flexible deployment shaft to exit the tube distal opening in a generally lateral direction with respect to the orientation of the introducer tube.

28. The device for marking a particular tissue area as recited in claim 24, wherein said introducer tube is comprised of a rigid material.

29. The device for marking a particular tissue area as recited in claim 28, and further comprising an introducer needle mount for holding said introducer tube as it is guided into the body.

30. A marker element applier for applying a marker element to a particular tissue area in order to mark said area for a later diagnostic or therapeutic procedure, comprising:
    a marker element;
    a flexible deployment shaft having a lumen, a distal end, and a proximal end;
    a squeeze handle; and
    a pull wire attached to said handle, the wire extending distally through the lumen of a flexible deployment shaft, a distal end of the pull wire being attached to said marker elemental;
    wherein said handle is actuated by a squeezing action to cause a proximal pulling force to be exerted on said pull wire.

31. The device for marking a particular tissue area as recited in claim 30, wherein said marker element has a width of less than 0.1 inches.

32. The device for marking a particular tissue area as recited in claim 31, wherein said marker element has a maximum width within a range of 0.030–0.050 inches.

33. A marker element applier for applying a marker element to a particular tissue area in order to mark said area for a later diagnostic or therapeutic procedure, comprising:
    a marker element;
    a flexible deployment shaft having a lumen, a distal end, and a proximal end;
    a handle; and
    a pull wire attached to said handle, the wire extending distally through the lumen of a flexible deployment shaft, a distal end of the pull wire being attached to said marker element, wherein the marker element and the pull wire are comprised of a single piece of sheet material.

34. The device for marking a particular tissue area as recited in claim 33, and further comprising a forming die disposed proximally of said marker element, the marker element comprising first and second legs and the forming die comprising first and second forming faces corresponding to each of said first and second legs, such that when said pull wire is pulled in a proximal direction, said first and second legs are pulled proximally against said first and second forming faces of said forming die.

35. The device for marking a particular tissue area as recited in claim 34, and further comprising a predesigned failure point disposed in the distal end of said pull wire, just proximal to said marker element, wherein when the pull wire is pulled in a proximal direction, said first and second legs are pulled proximally against said first and second forming faces such that said legs close inwardly toward one another, attaching to adjacent tissue to be marked as they close, the proximal pulling force on said pull wire causing said predesigned failure point to yield when said marker element is attached to said tissue so that said marker element and said pull wire become separated from one another.

36. The device for marking a particular tissue area as recited in claim 33, and further comprising a predesigned failure point disposed in the distal end of said pull wire, just proximal to said marker, said failure point being adapted to fail, separating said marker element from said pull wire, upon application of a predetermined pulling force on said pull wire.

37. The device for marking a particular tissue area as recited in claim 33, wherein said single piece of sheet material comprises rectangular stock.

38. The device for marking a particular tissue area as recited in claim 37, wherein said rectangular stock is twisted.

39. A method of marking tissue in a body to identify a selected location for a diagnostic or therapeutic procedure, the method comprising:
    manipulating an introducer tube into said body, so that a distal end of the introducer tube is disposed at said selected location;
    inserting a flexible deployment shaft of a flexible marker element applier into a lumen of said introducer tube, such that a distal end of said deployment shaft exits the introducer tube through a distal opening in the tube;
    pulling proximally on a pull wire extending through a lumen of said deployment shaft, the pulling action on said wire causing a marker element to disengage from said marker element applier and lodge in tissue at said selected location.

40. A device for marking a particular tissue area within a body to identify said particular tissue area for a later diagnostic or therapeutic procedure, comprising:
    a marker element;
    an apparatus for remotely delivering said marker element from outside the body to the particular tissue area, comprising an introducer having a tube and a longitudinal axis, wherein the tube has a lumen, a distal opening oriented with respect to the longitudinal opening, and a proximal hub and a flexible tube insertable into said introducer, said flexible tube having means to apply said marker element to said particular tissue area.

41. The device for marking a particular tissue area as recited in claim 40, wherein the distal end of said introducer tube is adapted for piercing and entering said body, such that the distal opening thereof is disposed adjacent to said particular tissue area.

42. The device for marking a particular tissue area as recited in claim 41, and further comprising an angled ramp disposed at the distal end of the introducer tube, adjacent to the distal opening on said tube, said ramp functioning to cause said flexible deployment shaft to exit the tube distal opening in a generally lateral direction with respect to the orientation of the introducer tube.

43. A device for marking a particular tissue area within a body to identify said particular tissue area for a later diagnostic or therapeutic procedure, comprising:

a marker element;

a flexible marker element applier for remotely delivering said marker element from outside the body to the particular tissue area, comprising an introducer having a tube comprised of a flexible material, wherein the tube has a lumen, a distal opening, and a proximal hub, the applier further comprising a flexible deployment shaft having a lumen, a distal end, and a proximal end;

the flexible deployment shaft being insertable though the lumen of said introducer tube for transporting said marker element to said particular tissue area;

said device further comprising a rigid annular conduit having a distal opening, said rigid annular conduit being adapted for entry into said body using an aided visualization device, wherein the distal opening of the conduit is able to be disposed adjacent to said particular tissue area, said flexible introducer tube being insertable into said rigid annular conduit such that the distal end of the flexible introducer tube exits said rigid annular conduit through the distal opening thereof, thereby transporting said marker element to said particular tissue area.

44. The device for marking a particular tissue area as recited in claim 43, wherein said rigid annular conduit comprises a biopsy power driver and probe.

45. A device for marking a particular tissue area within a body to identify said particular tissue area for a later diagnostic or therapeutic procedure, comprising:

a marker element;

a flexible marker element applier for remotely delivering said marker element from outside the body to the particular tissue area, comprising an introducer having a tube comprised of a flexible material, wherein the tube has a lumen, a distal opening, and a proximal hub, the applier further comprising a flexible deployment shaft having a lumen, a distal end, and a proximal end;

the flexible deployment shaft being insertable though the lumen of said introducer tube for transporting said marker element to said particular tissue area;

an angled ramp disposed at the distal end of the flexible introducer tube, adjacent to the distal opening on said tube, said ramp functioning to cause said flexible deployment shaft to exit the tube distal opening in a generally lateral direction with respect to the orientation of the introducer tube.

* * * * *